United States Patent [19]

Zaidi

[11] 4,197,947
[45] Apr. 15, 1980

[54] STERILE PACKAGE

[75] Inventor: Syed M. H. Zaidi, Philadelphia, Pa.

[73] Assignee: Paper Manufacturers Company, Southampton, Pa.

[21] Appl. No.: 31,504

[22] Filed: Apr. 19, 1979

[51] Int. Cl.² ............................................. B65D 85/54
[52] U.S. Cl. .................................... 206/438; 206/459; 206/807
[58] Field of Search ..................... 206/459, 438, 807; 126/234, 119, 114 AJ, DIG. 41; 428/201, 207, 211; 40/359, 360, 312, 306

[56] References Cited

U.S. PATENT DOCUMENTS

| 3,460,742 | 8/1969  | Langdon ............................ 206/459 |
| 3,527,400 | 9/1970  | Shepherd et al. .................... 206/459 |
| 3,533,548 | 10/1970 | Taterka ............................... 206/459 |
| 3,547,257 | 12/1970 | Armentrout . |
| 3,616,898 | 11/1971 | Massie ............................... 206/459 |
| 4,097,236 | 6/1978  | Daly et al. . |
| 4,121,714 | 10/1978 | Daly et al. ......................... 206/459 |
| 4,165,002 | 8/1979  | Meagher ........................... 206/459 |

Primary Examiner—Joseph Man-Fu Moy
Attorney, Agent, or Firm—Howson and Howson

[57] ABSTRACT

A package for encasing a sterile medical product. This package is formed of overlying front and rear panels of transparent plastic sheet material at least one of which has applied thereto an adhesive coating which is opaque. The panels are joined along their edges by a rupturable heat seal formed of the adhesive, the heat seal being transparent, but becoming opaque in those areas where it is ruptured.

5 Claims, 4 Drawing Figures

STERILE PACKAGE

The present invention relates to improved packages for containing medical or hospital supplies and keeping them sterile until use. This invention includes a unique seal capable of maintaining the sterility of the contents of the packages, but which can be readily broken for removal of the sterile contents within. The presence of the seal is indicated by its transparency, which, upon being ruptured, becomes opaque.

BACKGROUND OF THE INVENTION

Medical and hospital supplies have been packaged and then sterilized to reduce the hazard of infection in hospitals and clinics. Packages previously employed have suffered from various disadvantages. Some of the packages have been difficult to open, requiring tearing or cutting of the packaging material. Other packages have the disadvantage that they are sealed by means of pressure-sensitive adhesives which permit the package to be opened and then resealed merely by pressing the adhesive-coated surfaces together. The pressure-sensitive seals are such that it cannot be readily determined by visual observation whether the seal has been broken whereby the contents may have been contaminated by air borne bacteria. In other prior known packages, the seal is such that it cannot be determined by simple visual inspection whether the seal is complete and impermeable to bacteria or whether the seal may have been broken in handling prior to use.

More recently sterile packages have been designed whereby the validity of a heat seal can be ascertained visually. Thus, U.S. Pat. No. 3,533,548 discloses a method for determining visually whether or not a certain area of a plastic film or sheet is securely sealed to an adjacent paper backing by coloring the plastic film in a relatively light shade of a selected color and heat sealing the sheets together. The sealed areas appear much darker than unsealed areas and thus a gap or interruption in the seal can be observed visually. Similarly, according to U.S. Pat. No. 4,097,236 a break in the heat seal between a clear plastic member and a paper member can be detected visually by coloring the paper member. If there is a break in the heat seal, the clear plastic member takes on an opaque appearance in the area of the broken seal.

A major drawback of the means for determining failure of the heat seal according to the above-discussed patents resides in the fact that inspection of the seal in many instances will require inverting the packages since the seal is visible only on one side of the package. Such procedure can very well interfere with high speed assembly line production of packages required to today's economy.

The package of the present invention overcomes these objections and drawbacks and comprises broadly a pair of front and rear panels made of nonporous transparent plastic sheet material, e.g. a polyolefin material such as polyethylene, which are sealed together about their peripheral edges to define a recess or pocket for holding the contents. Prior to being heat sealed together one or both of the panels is coated, at least in those areas which are to be heat sealed, with an adhesive, which, after application and drying, is opaque. Upon being subjected to heat and pressure in the seal area, the adhesive becomes transparent, whereby the presence of an integral seal which is impermeable by bacteria is readily determined by mere visual observation from either side of the package. When the heat seal is ruptured, as for example in opening the package, the seal areas on both the front and rear panels become opaque. Thus, this invention provides means for determining whether the seal is incomplete or has been ruptured whereby air borne bacteria may have contaminated the contents.

The invention will now be described in greater detail in conjunction with the accompanying drawings in which.

Figure 1:
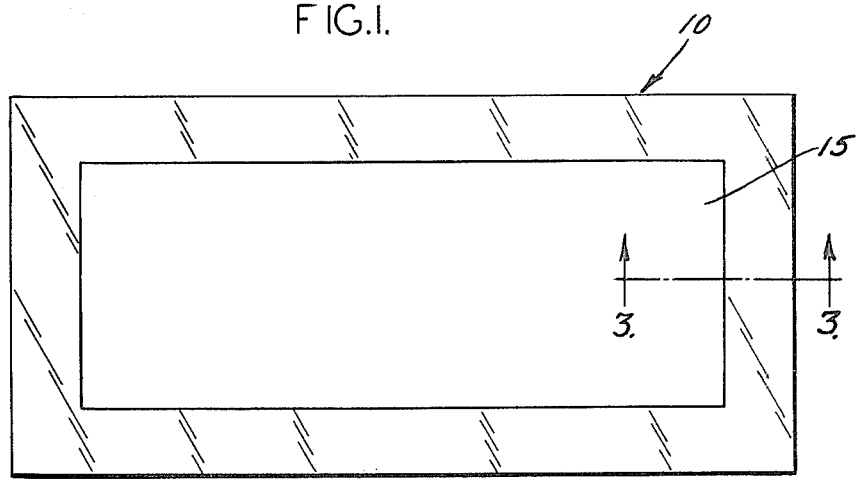
FIG. 1 is a top plan view of a package showing the transparent adhesive seal between the front and rear members of the package.
Figure 2:
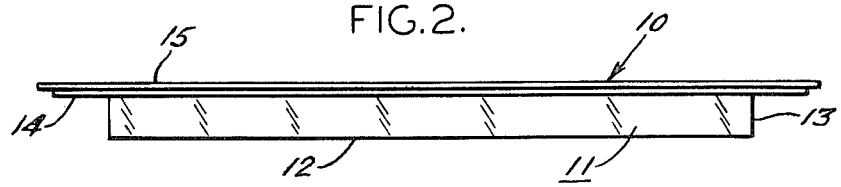
FIG. 2 is a side elevation of the package of FIG. 1.

In FIGS. 1 and 2, a tear-open package 10 completely encases a sterile article, not shown, which for example might be a hypodermic syringe. The package comprises a generally rectangular tray 11 of nonporous transparent polyolefin sheet material. Tray 11 has a relatively flat bottom 12, a shallow rim 13, extending outwardly from which is a peripheral flange 14. Overlying the tray 11 is a sheet 15, also of nonporous, transparent polyolefin material. Sheet 15 is substantially coextensive with tray 11 so that the peripheral portions of the sheet overlie the flange 14 of tray 11. Preferably, at least one edge 16 (FIG. 3) of sheet 15 extends beyond the flange 14 of tray 11 so that the sheet can be grasped by the user to aid in removal of the sheet to obtain access to the sterile article within the package.

Figure 3:
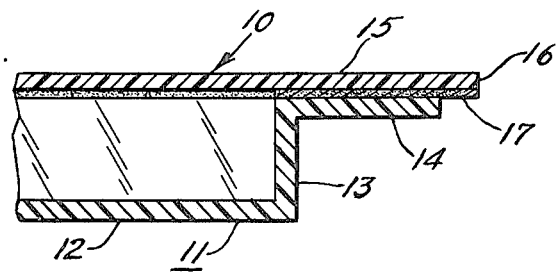
FIG. 3 is an enlarged fragmentary cross-sectional view taken along the line 3—3 of FIG. 1.

Applied to the surface of the sheet 15 which faces on the tray 11 is a layer of an adhesive material 17 (see FIG. 3). This adhesive coating, after being applied to sheet 15 and dried, is relatively opaque since the adhesive coating comprises a layer of small particles of a thermoplastic material, which particles scatter light to render the adhesive coating opaque. When sheet 15 is superimposed on tray 11 and those portions of sheet 15 which overlie flange 14 of tray 11 are subjected to heat and pressure to bond the sheet to the tray, the thermoplastic particles of the adhesive coating 17 fuse and flow together. The result is a transparent heat seal in the flange area 14 of tray 11. The contents of the sealed package can be sterilized as for example by radiation.

Figure 4:
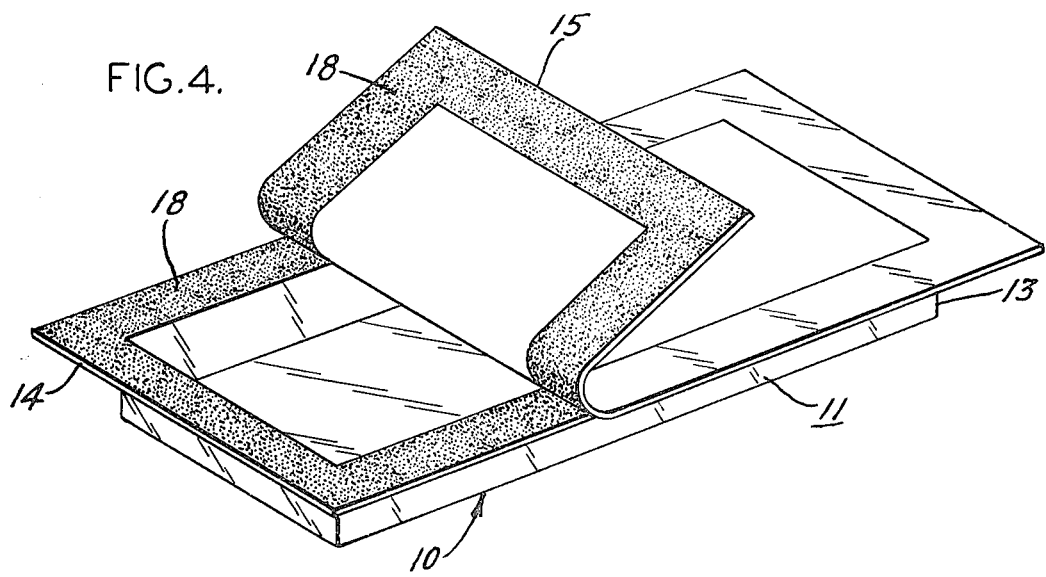
FIG. 4 is a perspective view of the package of FIG. 1 partially opened.

Referring particularly to FIG. 4, when the heat seal between tray 11 and sheet 15 is broken, as for example by peeling back sheet 15, the adhesive layer in those areas of the flange 14 of tray 11 and of Sheet 15 where the heat seal has been broken become opaque (see areas 18 of FIG. 4). Thus, a particular advantage of the sterile package of this invention is that the integrity of the heat seal can be determined readily through visual inspection from either side of the package. Should any portion of the peripheral heat seal be opaque, then it can be recognized that the heat seal has been broken and that the contents of the package are no longer sterile.

Suitable adhesive coatings for use in the sterile package of this invention may be applied in the form of thermoplastic polymer latexes, typical examples of which are latexes containing such thermoplastic copolymers of ethylene and vinyl acetate and vinyl acrylate copolymers. A particularly preferred latex coating composition has the formulation set forth in Table I, below:

TABLE I

| Constituent | Weight Percent | |
| --- | --- | --- |
| | Wet Basis | Dry Basis |
| Ethylene vinyl acetate copolymer* | 27.6 | 24.4 |
| Vinyl acrylic copolymer latex** | 18.4 | 20.3 |
| Octadecamide*** | 18.4 | 40.7 |
| Alpha Pinene resin**** | 5.2 | 11.6 |
| Alkyl aryl***** polyester alcohol | 1.3 | 2.9 |

*Elvax 1122 D. E. I. duPont
**Hycar 2600-X-137, B. F. Goodrich Co.
***Armid 18, Armour and Co.
****Piccolyte A-100, Hercules, Inc.
*****Triton X-100, Rohm and Haas Co., Inc.

The adhesive coating 17 may be applied to sheet 15 using standard coating equipment, a typical example being a roller coater. The amount of coating applied should be sufficient to provide an air-tight seal between the tray 11 and sheet 15. It has been found that adhesive coating when applied at the rate of 5 pounds adhesive (dry basis) per 475000 ft.$^2$ of sheet provides a heat seal which, although it can be readily ruptured by peeling back sheet 15, nevertheless, is air tight and maintains its integrity in ordinary handling of the package.

A further understanding of the invention will be had from the following examples:

EXAMPLE 1

The several constituents of which the coating composition of which Table I is comprised were placed in a Unicon Process, Inc. Model 01 Attritor containing 900 g. of ⅛ in. diameter stainless steel shot, and the attritor was then run at maximum speed. The resulting coating was then applied to the polyethylene surface of a web comprising a superimposed layer of 0.48 mil. polyester film laminated to a 2 mil. medium density polyethylene film using a #12 wire wound rod. The film was dried in an oven at 180° F. for 2 minutes. On removal from the oven, the coating had an opaque matte, white-appearing surface.

The coated film was heat sealed to a 20 mil. polyvinylchloride film using a Sentinal Model 12AS heat sealer, the sealing conditions being 275° F., 40 psi and a dwell time of 2 seconds. The area of the coating which was heat sealed became transparent, the remainder of the coating remaining opaque. On peeling, the bond was found to be uniform and strong, but the transparent seal area on the polyethylene surface again became opaque as did the surface of the polyvinylchloride film which had been heat sealed.

EXAMPLE 2

The procedure of Example 1 was repeated except that the dwell time in forming the heat seal was 0.5 seconds and both layers were the polyethylene/polyester laminate sheet material of Example 1. The seal was transparent, but on peeling or destruction of the seal, the seal areas of both layers became white.

The plastic sheet material which may be used in fabricating the sterile packages of this invention may be formed of a number of different thermoplastic polymers in addition to polyolefins, examples thereof being polystyrene, polyvinylchloride thermoplastic acrylic multipolymer and polycarbonate.

Although this invention has been described in particular with respect to a package in the form of a sealed rectangular tray, the invention contemplates other configurations and constructions which take advantage of the novel transparent heat seal of the invention.

It is claimed:

1. A package for containing a sterilized article comprising a container made of front and rear panels of nonporous, transparent plastic material, said panels being joined together about their peripheral edges by means of a transparent seal to define a recess for holding a sterilized article, said seal between said panels being provided by an adhesive which upon application to one or both of said panels is opaque, but transparent to provide such transparent seal, said adhesive forming said seal becoming opaque in those areas of said front and rear panels where said seal has been ruptured.

2. A package according to claim 1 in which said adhesive coating comprises a thermoplastic polymer applied in latex form.

3. A package according to claim 1 in which one of said panels comprises a tray having a rim with a peripheral flange extending outwardly therefrom, to which flange said opposing panel is heat sealed about its periphery.

4. A package according to claim 3 in which said tray is formed of polyvinylchloride and the panel heat sealed thereto is formed of a polyolefin.

5. A package according to claim 4 in which said polyolefin panel comprises polyethylene.

* * * * *